United States Patent [19]

Micheron et al.

[11] Patent Number: 5,029,336
[45] Date of Patent: Jul. 2, 1991

[54] COMPUTER-AIDED TOMOGRAPHY APPARATUS

[75] Inventors: Francois Micheron, Gif sur Yvette; Sylvain Kretschmer, Paris; Jean C. Lehureau, St. Genevieve des Bois; Francois Zinger, Fontenau aux Roses; Michel Hommerin, Savigny sur Orge, all of France

[73] Assignee: Thomson-CGR, Paris, France

[21] Appl. No.: 309,791

[22] PCT Filed: Jun. 26, 1987

[86] PCT No.: PCT/FR87/00249

§ 371 Date: Jan. 3, 1989

§ 102(e) Date: Jan. 3, 1989

[87] PCT Pub. No.: WO88/00025

PCT Pub. Date: Jan. 14, 1988

[30] Foreign Application Priority Data

Jul. 7, 1986 [FR] France .................. 86 09835

[51] Int. Cl.5 .................................. A61B 1/00
[52] U.S. Cl. ............................. 378/4; 378/19
[58] Field of Search ........................ 378/4, 19

[56] References Cited

U.S. PATENT DOCUMENTS

| 4,109,998 | 8/1978 | Iverson | 350/23 |
| 4,259,584 | 3/1981 | Krumme et al. | 378/15 |
| 4,323,781 | 4/1982 | Baumann et al. | 378/4 |
| 4,593,400 | 6/1986 | Mohyen | 378/99 |
| 4,845,769 | 7/1989 | Burstein et al. | 378/58 |

FOREIGN PATENT DOCUMENTS

| 3019132 | 11/1981 | Fed. Rep. of Germany . |
| 3530939 | 3/1987 | Fed. Rep. of Germany . |
| 2338455 | 8/1977 | France . |
| 2440041 | 5/1980 | France . |

Primary Examiner—Carolyn E. Fields
Assistant Examiner—David P. Porta
Attorney, Agent, or Firm—Oblon, Spivak, McClelland, Maier & Neustadt

[57] ABSTRACT

The apparatus comprises an X-ray source (6) to generate a beam of radiations (7) through an object (4) or the body of a patient to be examined and a multichannel detector (8) to provide information concerning the intensity of the radiation retransmitted by the object examined. Both the source and the detector are mounted on a rotor (2) integral with the stator (1) which surrounds the object (4) examined. It also comprises at least one lateral diffusion light guide (14, 15) wound round the rotor (2) or on the internal surface of the stator (1) to transmit optically between optical receiver and emitter means (9, 10) of the rotor (2) and corresponding optical means (16, 17) of the stator (1), the information provided by the multichannel detector (8) and the control information of the X-ray source (6).

1 Claim, 4 Drawing Sheets

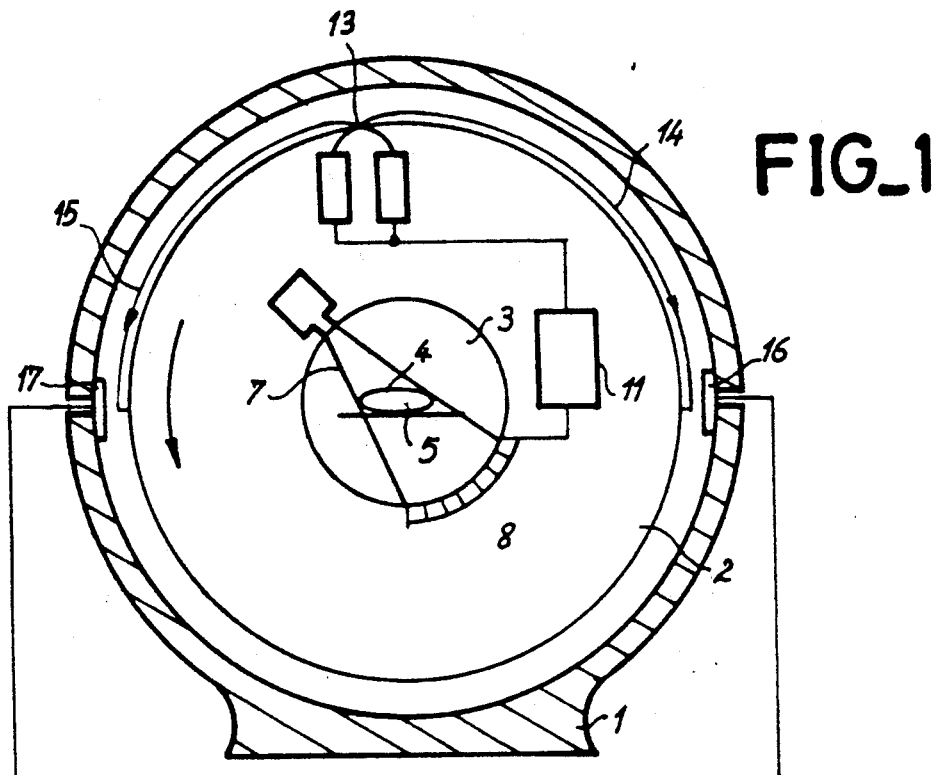
FIG_1
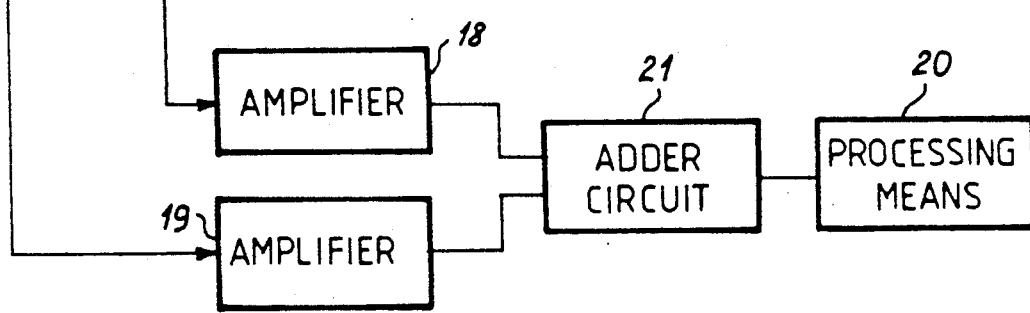
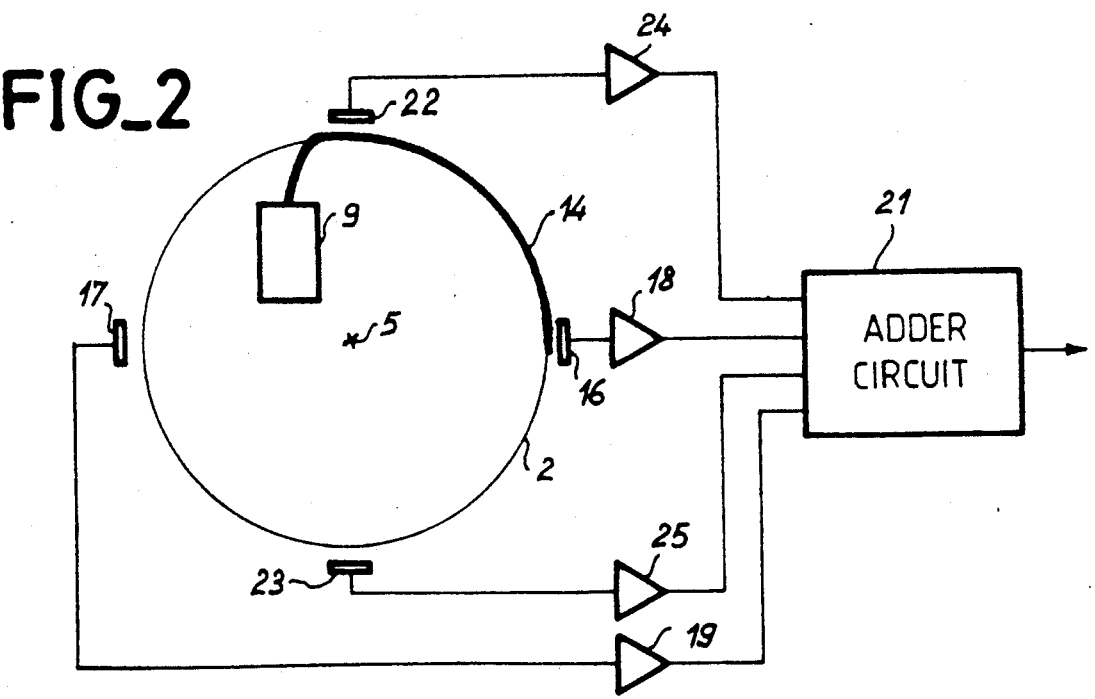
FIG_2

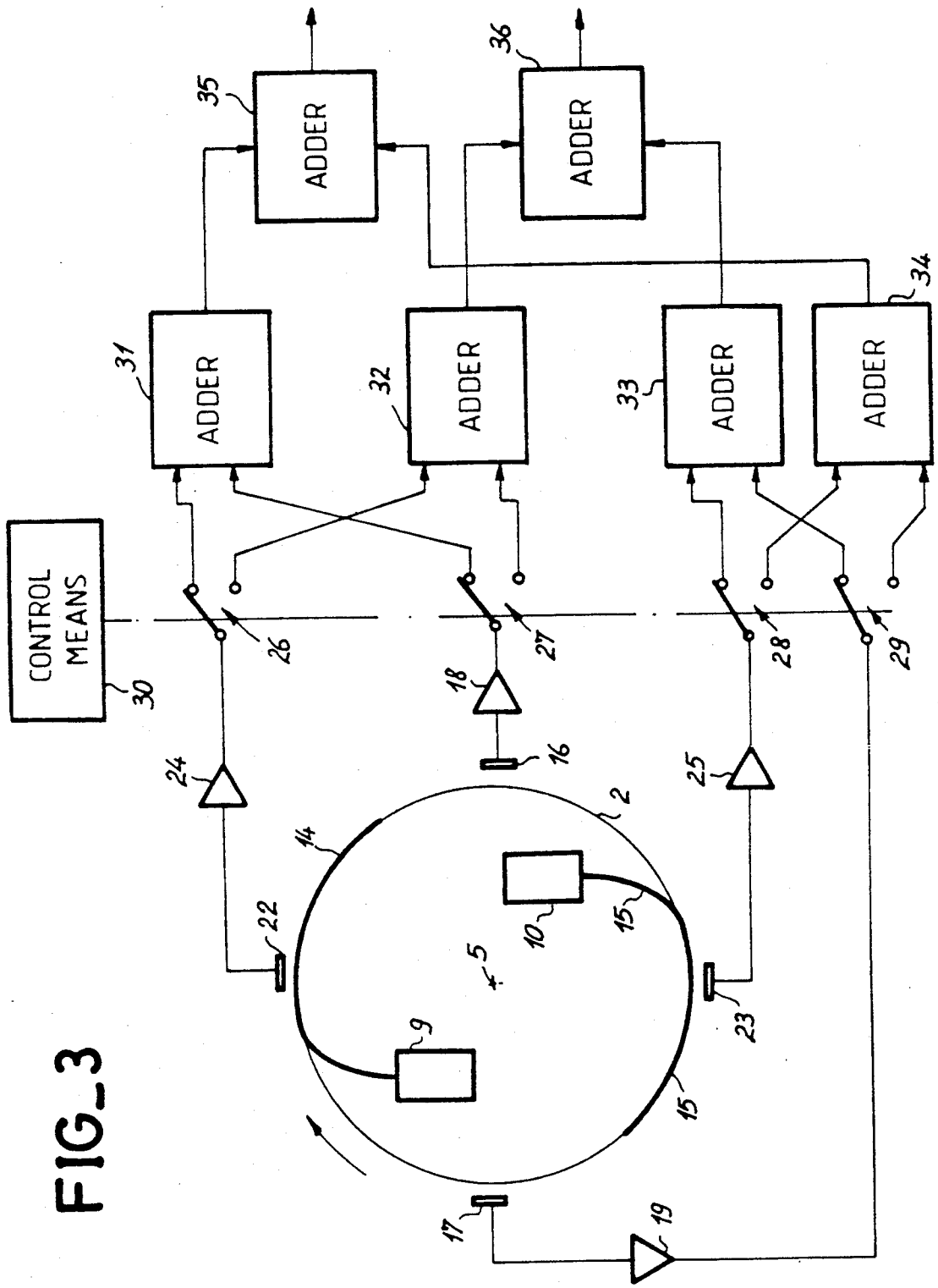
FIG_3

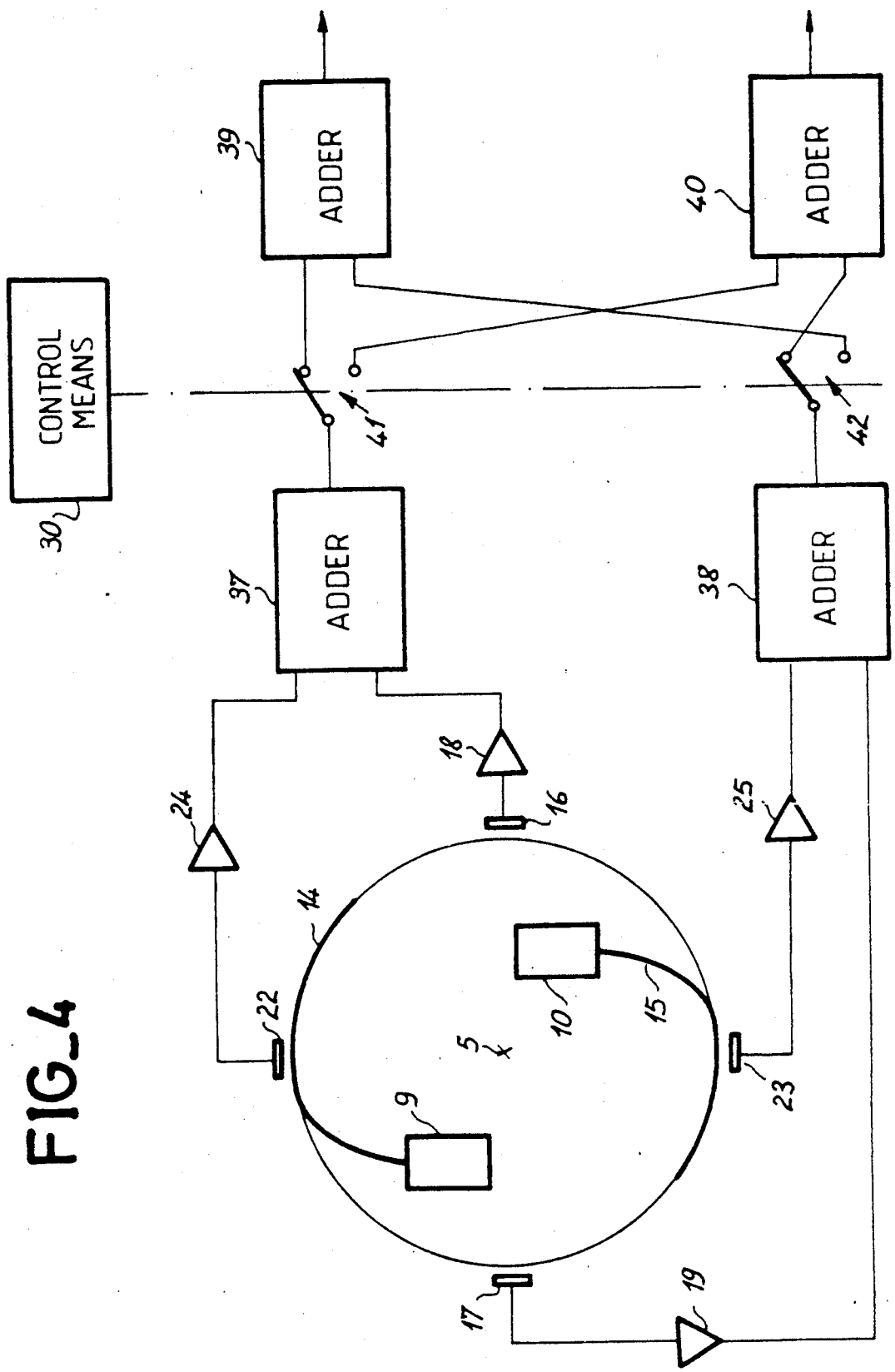

FIG_5
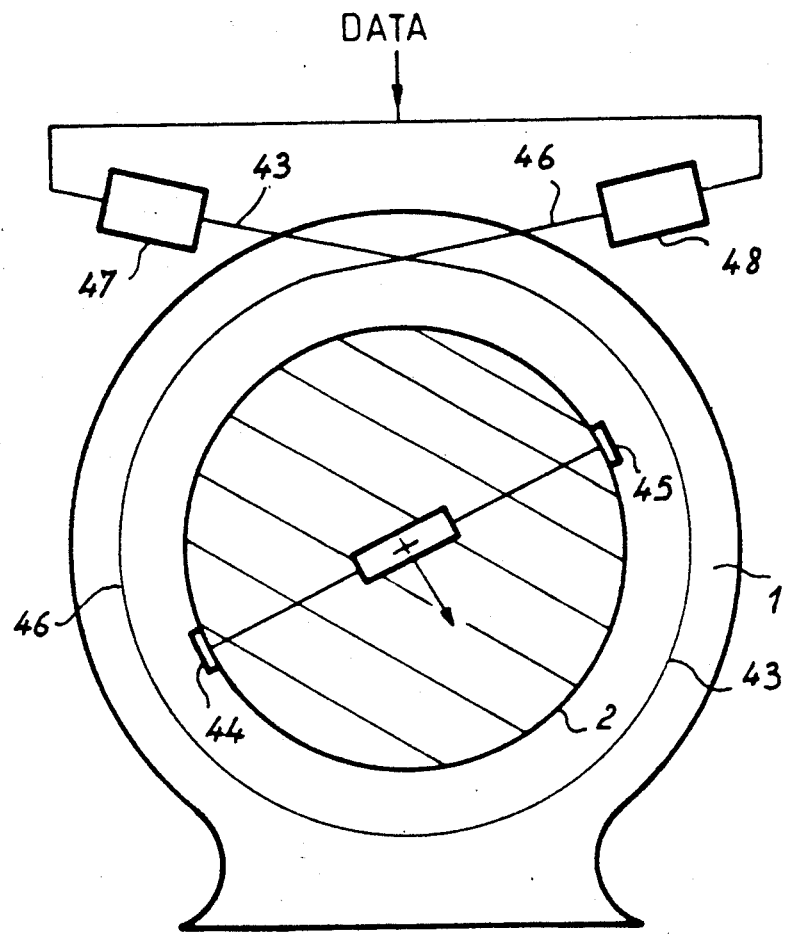
FIG_6
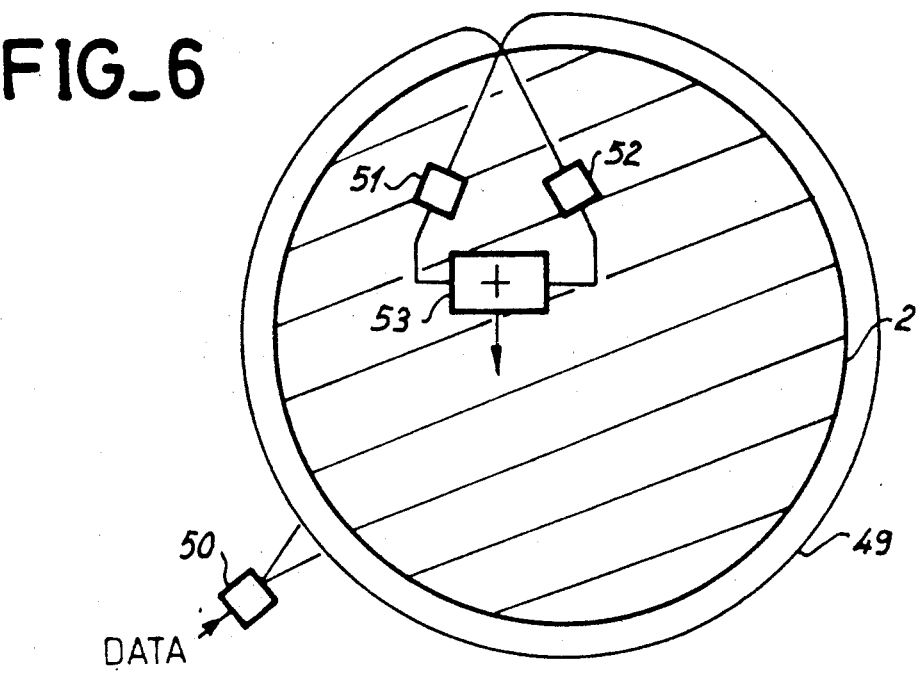

COMPUTER-AIDED TOMOGRAPHY APPARATUS

The present invention relates to a computer-aided tomography apparatus for obtaining transverse tomographic scans in a very rapid manner.

In known tomographic devices, provision is made for an x-ray source fed by a high-voltage supply which generates a very narrow x-ray beam in the direction of an object or of the body of a patient to be examined. This beam passes through the object or the patient's body before being intercepted and measured by a multichannel detector. The assembly consisting of x-ray source and multichannel detectors is mounted on a turntable or rotor which rotates about the object under examination within a frame or stator. The signals delivered by the multichannel detectors are transmitted to the data-processing device or external computer so as to form an image of each of the object slices thus examined.

In these devices, supply of power to the x-ray source and transmission of the signals delivered by the multichannel detectors are ensured by means of electric cables guided by a winding device constructed for example in the manner described in French Pat. Nos. 2,455,451 and 2,385,632.

However, the presence of these cables has an adverse effect on the speed of performance of these devices since it limits the displacements of the rotor and imposes for each rotation stages of acceleration and braking which increase the tomographic examination times to no useful purpose.

The aim of the invention is to overcome the disadvantages mentioned in the foregoing.

To this end, the invention has for its object a computer-aided tomography apparatus comprising an x-ray source for generating a radiation beam through an object or through the body of a patient to be examined and a multichannel detector for providing information relating to the intensity of radiation retransmitted by the object under examination, both source and detector being mounted on a rotor integral with a stator which surrounds the object being examined, characterized in that it comprises at least one lateral diffusion light guide wound around the rotor or on the internal surface of the stator so as to transmit optically, between optical emitter and receiver means of the rotor and corresponding optical means of the stator, the information delivered by the multichannel detector and the control information of the x-ray source, the assembly being so arranged as to ensure that on the one hand each optical emitter is in a fixed position relatively to one end of a light guide in order to cause the information to be transmitted to penetrate through said end and that, on the other hand, each receiver in relative motion with respect to a light guide receives the information by lateral diffusion of light through the external surface which surrounds the longitudinal axis of the light guide.

The invention has an advantage in that it permits rotations of the rotor without discontinuity in the same direction of rotation about the object or the body of the patient under examination. It thus eliminates the dead periods in examinations which were due to stages of acceleration and braking of tomographic devices of the cable transmission type. By virtue of the fact that it makes use of light guides, the invention also permits optical transmissions at high bit rates exceeding 10 Mbits/s, thus making it possible to obtain image reconstructions by means of the external data-processing units in very short periods of time.

Other characteristics and advantages of the invention will hereinafter become apparent from the description given with respect to the accompanying drawings, in which :

FIG. 1 illustrates a tomographic apparatus in accordance with the invention, comprising means for optical transmission of information between at least one emitter attached to the rotor and light receivers attached to the stator.

FIGS. 2 to 4 illustrate different alternative forms of construction of the transmission means of FIG. 1.

FIGS. 5 and 6 illustrate different embodiments of the invention which permit optical transmission of information between an emitter attached to the stator and light receivers attached to the rotor.

The tomographic apparatus which is illustrated in FIG. 1 comprises a frame 1 or stator within which rotates a turntable or rotor 2. The rotor 2 is pierced at its center by a hole 3 of sufficient size to allow the body 4 of a patient to be examined to be placed within the interior. The rotor and the stator are centered coaxially on an axis 5 which is perpendicular to the plane of the figure. The rotor 2 supports a radiation source 6, the fan beam 7 of which illuminates through the patient's body 4 multichannel detectors 8 which are also supported by the rotor 2 and located in FIG. 1 at the periphery of the hole 3 in a direction diametrically opposite to that of the source 6 with respect to the axis 5.

The rotor 2 also has two optical emitters constituted by light sources having the form for example of laser diodes 9 and 10 of a few mW which are modulated simultaneously by the multichannel detectors 8 through a modulator 11.

The laser diodes 9 and 10 are coupled respectively to one end of first and second lateral diffusion light guides 14 and 15 wound on the rotor each over a length of ¼ of a turn in two opposite directions from the same point of origin 13 of the periphery of the rotor so that the sum of lengths of the two guides wound on the rotor should make one half-turn without interruption.

Optical receivers or detectors 16 and 17 are placed at two diametrically opposite points on the internal periphery of the stator 1 so as to collect the light diffused laterally by each of the guides. Signal amplifiers 18 and 19 connect respectively optical detectors 16 and 17 to processing means 20 which may be constituted by a computer via an adder circuit 21.

In this configuration, since each of the light guides 14 and 15 has a length of ¼ of a turn, one light guide is always located opposite to one of the two light detectors 16 or 17, irrespective of the position of the rotor 2 relative to the stator 1. In consequence, irrespective of the positions of the rotor 2, the detectors 16 and 17 collect in alternate sequence the signals delivered by the multichannel detectors 8 and diffused simultaneously by the light guides 14 and 15.

For the good performance of the invention, the light sources 9 and 10 are preferably constituted by solid-state lasers. By way of example, taking into account the bit rate of 10 Mbits/s and the light powers which are necessary, lasers such as the type HLP 1600 produced by Hitachi and having a power rating of $P_o = 15$ mW, or the type TXSK 2101 produced by Telefunken and having a power rating of $P_o = 10$ mW, are suitable. Preferably, the light guides will be formed by optical fibers and, in this case, the spatial extension of the light sources 9 and 10 around the stator ring is obtained by lateral diffusion of these fibers. These fibers are preferably plastic fibers such as the type known under the reference Plastifo T 301 marketed by the French law company Optectron or under the reference ESKA-C marketed by the Japanese law company Mitsubishi.

The power radiated laterally by these fibers over a length of 1 cm is typically 2 to $5 \times 10^{-5}$ Po, that is, 20 to $50 \times 10^{-9}$ W where Po $= 10^{-3}$ W.

By virtue of the fact that this diffusion is the natural diffusion of the fiber, it may be considered as constant, at least over lengths of a few meters.

The detectors 16 and 17 can be constituted by silicon photodiodes.

Under these conditions, since the energy necessary for detection of 1 bit by a silicon photodiode illuminated over an area of a few mm² can be estimated at approximately $10^{-14}$ joule, the maximum possible bit rate to be expected will be:

$$D_{max} = \frac{2.5 \times 10^{-8}}{10^{-14}} = 2 \text{ to } 5 \text{ Mbits/s}$$

by collecting the light diffused laterally to the fiber over 1 cm of this latter throughout the space.

In practice, said bit rate can be increased to 10 Mbits/s by artificially increasing the natural diffusion of the fibers and by making use, for example, of diodes known under the reference BPW 34 produced by the Siemens Company associated with low-noise preamplifiers such as the amplifier known under the reference SL 550 produced by the Pleyssey Company. There is obtained under these conditions a sufficient signal-to-noise ratio of the order of 4 at the amplifier output in respect of an incident power of a few microwatts on the photodiodes of the detectors 16 and 17.

These results can be obtained, for example, by adjusting the power of the laser to typically $10 \times 10^{-3}$ W by collecting at the level of the detectors 16 and 17 the light diffused by each of the fibers throughout the space by means of a suitable optical collection system and by increasing the lateral diffusion of the fiber.

The first two points do not offer any particular difficulties.

In regard to the last point, it will be possible to increase the normal lateral diffusion of a fiber by a factor within the range of 10 to 1000 by modifying the structure of this latter over a predetermined zone of its surface.

When a light ray passes through the fiber, the heterogeneity of material obtained in this zone causes on the one hand reflections which interfere with the light path and on the other hand the exit of the light rays through the surface element of the fiber which covers the modified zone.

In order to obtain this structural modification, a number of mechanical, physico-chemical or chemical methods can be employed independently of each other or if necessary in a complementary manner. From a mechanical standpoint, the structural modification can be obtained for example, in the case of clad-core fibers, by producing a local reduction in thickness of the cladding which surrounds the core by scraping, grooving or any other equivalent mechanical process or else by irreversibly modifying the cross-section of the fiber, if necessary by rolling.

From a physico-chemical standpoint, it will be possible to include elements of solid powder, metal powder, abrasives and the like in the core of the fiber at the moment of fabrication or else to mix in the diffusion zone immiscible polymers such as, for example, polystyrene with methyl polymethacrylate.

From a chemical standpoint, it will be possible to carry out solvent etching of the fiber surface which covers the diffusion zone.

These different methods result in the creation of a flaw which, if it is constant per unit of length along the entire fiber, produces an intensity of light diffused at each point along a fiber which decreases as an exponential function of the distance between the point considered and the light source which excites the fiber. The result thereby achieved is that, in a given application, the utilizable length of a fiber in accordance with the invention will depend on the power of the source, on the sensitivity of the photodetector as well as on the type of diffusing process applied to the fiber.

Although these different methods are conducive to collection of the diffused light by photodiode, it is also clear that losses within the fibers thus modified are considerably increased and that the useful length of a fiber is consequently reduced. In this connection, it will be possible to determine the maximum usable length of a fiber by assuming as a first approximation that the entire attenuation within the fiber is due to lateral diffusion. Since at any point of abscissa x of an optical fiber the light power P(x) transported by the fiber can be defined by a relation of the form $$P(x) = Po \exp{-\alpha x}$$

where Po is the optical power of the light beam introduced at the entrance of a fiber, the loss by diffusion over a short distance $dx = 1$ then has the value $$\frac{d P(x)}{dx} = \frac{p(x)}{1} = \alpha\, Po \exp - \alpha x$$

There is thus defined the length $x_{omax}$ such that, at this abscissa, $p(x) = \eta \cdot Po$, that is, the diffusion power which can still be utilized.

By developing the calculations, we obtain:

$$x_{omax} = \frac{1}{e \cdot \eta}$$

In other words, the maximum length of the fiber, on condition that it can be given the optimum attenuation, depends solely on 1 (length of collection of the diffusion), that is to say on the width of the photodiode (without optical collection system) and on the minimum attenuation ratio 0 between diffused power and emitted power.

By way of example, by setting the powers
Po = 10 mW and $P_{min}$ on a photodiode $= 4 \times 10^{-6}$ W with a collection of diffusion carried out on ⅓ of space (without optical system), the diffused power will be: $12 \times 10^{-6}$ W; hence $\eta = 1, 2 \times 10^{-3}$.

If $1 = 3$ mm is the width of the photodiode, the coefficient of optimum attenuation will be $$\alpha = \frac{e \cdot \eta}{1} = 1.1 \times 10^{-2} \text{ cm}^{-1} \text{ (9.5 dB/m)}$$

and the maximum length of the fiber will be $$x_{omax} = \frac{1}{\alpha} = 92 \text{ cm}.$$

Since the circumferences of the rotors of tomographic scanners usually have lengths at least equal to 3 meters, the foregoing calculation shows that the example of construction of FIG. 1 is wholly practicable with two optical fibers and two detectors.

However, the invention is not limited in its applications to rotor circumferences of less than three meters. In particular, it will be possible in the case of larger circumferences to increase the number of detectors distributed over the surface of the stator and to modify the transmission means of the embodiment of FIG. 1 in the manner illustrated schematically in FIG. 2 in which, in order to simplify the description, only the elements which are similar to FIG. 1 and essential to a good understanding of the diagram have been shown with the same references. In this figure, a single laser diode such as 9, for example, is coupled to a single optical fiber 14, the length of which corresponds to ¼ of a revolution. In this example, only four detectors 16, 17, 22 and 23 are necessary. These detectors are connected respectively to amplifiers 18, 19, 24 and 25, and the signals delivered by these amplifiers are applied to the corresponding inputs of an adder circuit 21 having four inputs.

Naturally, the example of construction of FIG. 2 can also be extended to other constructions in which provision is made only for a single source 9 coupled to a single fiber having a length equal to 1/N revolution of the rotor 2 and N detectors uniformly distributed over the entire circumference of the stator 1.

In addition, the transmission means of the embodiment of FIG. 1 can also be modified in the manner shown diagrammatically in FIG. 3 in which the elements similar to FIGS. 1 and 2 have been designated by the same references. In this figure, the two laser diodes 9 and 10 are located at diametrically opposite locations on the rotor 2 and the corresponding optical fibers 14 and 15 are wound in the same direction. The advantage of the transmission device shown is that it permits simultaneous transmission of data in parallel along the fibers 14 and 15. Two-position switches 26, 27, 28 and 29 are controlled simultaneously by control means 30 at each half-revolution of the rotor 2 for transmitting at favorable moments the data or information signals delivered by the detectors 16, 17, 22 and 23 via amplifiers 18, 19, 24 and 25 to corresponding inputs of adder circuits 31, 32, 33 and 34. Adder circuits 35 and 36 ensure addition of the signals delivered by the outputs of the adders 31 and 34 on the one hand, and 32 and 33 on the other hand. It will be possible to carry out synchronization of the control means 30 of the switches 26 to 29 with the angular position of the rotor 2 by means of optical sensors (not shown) placed between stator 1 and rotor 2. Naturally, this arrangement can also be extended to transmission means having N channels of parallel data, each channel being materialized as in FIG. 3 by a light source and an optical fiber.

In another alternative embodiment of the invention which is illustrated in FIG. 4, it will be noted that the diagram of FIG. 3 can be simplified even further by placing a first adder circuit 37 directly at the output of the amplifiers 18 and 24 and a second adder circuit 38 at the output of the amplifiers 19 and 25. At each half-revolution of the rotor 2, the output of the adder circuit 37 is connected alternately to a first input either of an adder circuit 39 or of an adder circuit 40 via a switch 41.

The output of the adder circuit 38 is connected alternately at each half-revolution of the rotor 2 to a second input either of the adder circuit 39 or of the adder circuit 40 via a switch 42. The signals of the first channel (optical fiber 14) are collected at the output of the adder circuit 39 and the signals of the second channel (optical fiber 15) are collected at the output of the adder circuit 40.

Although the examples of construction of FIGS. 1 to 4 have been described with transmission modes in which the data or information signals flow within light guides between rotor and stator, it will be understood without difficulty that, conversely, the same solution can also be employed for transmitting data or information signals between stator 1 and rotor 2. In this case, the emitter which is rigidly fixed to the stator will be constituted by a modulated optical source extended by one (or a number) of diffusing fiber(s) and the receiver will be constituted by one (or a number) of photodiode(s) rigidly fixed to the rotor. Taking into account the fact that, in this direction of transmission, the passband of the transmission support can be narrower than in the other direction, the necessary incident power on a silicon photodiode can be determined at approximately $100 \times 10^{-9}$ W.

By repeating the previous calculations, the maximum length of the fiber will then have the value in respect of $P_o = 10^{-3}$ W, $\eta = 10^{-4}$ and a collection of the diffusion over 3 mm in ⅛ of the space :

$$x_{omax} = \frac{1}{3e\eta} = 3.7 \text{ meters}$$

Moreover:
$$\alpha_{opt} = 3 \times 10^{-3} \text{ cm}^{-1} (\simeq 2.6 \text{ dB/m})$$

Consequently in this case, as shown in FIG. 5, a single fiber 43 wound within the stator may prove sufficient, provision being likewise made for a single detector on the rotor 2.

Nevertheless, this device or part of this device can be duplicated as a precautionary measure or if necessary in order to pass several channels without multiplexing, as shown in the arrangements of the fibers 43, 46 of the detectors 44, 45 and of the light sources 47, 48 in FIG. 5. It accordingly follows that all the previous diagrams apply in this case.

Moreover, taking into account the low power values employed in emission, it will also be possible to contemplate the use of electroluminescent diodes having very high efficiency instead of laser diodes.

However, it will also be possible to contemplate a second solution for transmission of information between stator or rotor.

This solution which is illustrated in FIG. 6 can consist in placing on the rotor 2 a scintillator element 49 constituted if necessary by a scintillating optical fiber which will be excited by a light source placed on the stator, this source 50 being modulated by the data to the information signals to be transmitted, for example, in order to control the x-ray source of the rotor.

The photons derived from scintillation within the fiber will be guided by this latter towards light detectors 51 and 52 which are rigidly fixed to the rotor 2 and connected to an adder 53.

By way of non-limitative example, it will be possible to employ as scintillating fiber a fiber known under the reference Plastifo 200 marketed by the French law company known as Optectron.

In this mode of utilization, in order to constitute the emitter 50, it will be possible to employ an electroluminescent diode which emits in the blue at a power level of approximately $40 \times 10^{-6}$ W. Assuming that $\frac{1}{4}$ of this power is absorbed in the fiber 49 and that the scintillation efficiency of this latter is 10% or in other words that 10% of this absorbed power propagates within the fiber, a power of approximately $10^{-6}$ W is obtained in the fiber in the emission zone. This power is also distributed within the fiber on each side of the emission zone. Since the lengths of absorption of this type of fiber are short, of the order of 1 meter ($\alpha \simeq 10^{-2}$ cm$^{-1}$), by establishing the minimum detectable light power within the fiber at $100 \times 10^{-9}$ W, it will be possible to determine for example the distance x, or a minimum of detection can also be obtained by applying the relation :

$$\frac{100 \times 10^{-9} \text{ W}}{500 \times 10^{-9} \text{ W}} = \exp - 10^{-2} x,$$

namely in the present case x = 1.6 meters.

On condition that a detector 51 or 52 is placed at each end of the fiber, the useful length of the fiber ($2 \times 1.6$ meters) appears under these conditions to be compatible with the circumference of the rotor.

In this case again, the principle can be extended to more than one source on the stator in a manner similar to the diagram of FIG. 2.

We claim:

1. A computer-aided tomography apparatus comprising:

an X-ray source for generating a radiation beam through an object or through the body of a patient to be examined;

a multichannel detector for providing information relating to the intensity of radiation transmitted through the object under examination wherein both said source and said detector are mounted on a rotor integral with a cylindrical stator which surrounds said object being examined, said tomography apparatus further comprising:

at least one lateral diffusion light guide wound around the rotor or on an internal surface of said cylindrical stator so as to transmit optically, between optical emitter means or optical receiver means of the rotor and respectively corresponding optical receiver means or optical emitter means of said stator, the information delivered by said multichannel detector or control information of the X-ray source, the assembly being so arranged as to insure that on the one hand said optical emitter means is in a fixed position relative to a first end of one of said at least one lateral diffusion light guide in order to cause the information to be transmitted to penetrate through said first end and that, on the other hand, receiver means in the relative motion with respect to one of said at least one lateral diffusion light guide receives the information by lateral diffusion of light through an external surface of said rotor having a cylindrical shape wherein said external surface surrounds a longitudinal axis of said at least one lateral diffusion light guide, whereby, in order to transmit the information of the multichannel detectors, the at least one lateral diffusion light guide is formed by single lateral diffusion optical fiber wound on the rotor over a length of $\frac{1}{4}$ of a turn and excited by a single light emitter, said guide further including four light receivers uniformly spaced on the internal surface of the stator.

* * * * *